United States Patent [19]

Takagi et al.

[11] Patent Number: 5,157,117
[45] Date of Patent: Oct. 20, 1992

[54] (6,7)-SUBSTITUTED-8-ALKOXY-1-CYCLO-PROPYL-1,4-DIHYDRO-4-OXO-3-QUINOLINECARBOXYLIC ACID-O3,O4) BIS (ACYLOXY-0) BORATE AND THE SALT THEREOF, AND THE PREPARING METHOD OF THE SAME

[75] Inventors: Naomi Takagi, Nogi; Hironobu Fubasami; Hiroshi Matsukubo, both of Okaya, all of Japan

[73] Assignee: Kyorin Pharmaceutical Co., Ltd., Tokyo, Japan

[21] Appl. No.: 724,164

[22] Filed: Jul. 1, 1991

[30] Foreign Application Priority Data

Jul. 6, 1990 [JP] Japan .................. 2-178765

[51] Int. Cl.$^5$ .................. C07F 5/02; C07F 5/04
[52] U.S. Cl. .................. 540/541; 544/62; 544/69; 544/229; 546/13
[58] Field of Search .................. 546/13; 540/541; 544/62, 69, 229

[56] References Cited

U.S. PATENT DOCUMENTS

| | | | |
|---|---|---|---|
| 4,874,764 | 10/1989 | Ueda et al. | 514/254 |
| 4,940,794 | 7/1990 | Hermecz | 546/13 |
| 4,997,943 | 3/1991 | Iwata | 546/13 |
| 5,091,530 | 2/1992 | Hermecz | 546/13 |

FOREIGN PATENT DOCUMENTS 241206 10/1987 European Pat. Off.
8807998 10/1988 World Int. Prop. O.

Primary Examiner—Mark L. Berch
Attorney, Agent, or Firm—Oblon, Spivak, McClelland, Maier & Neustadt

[57] ABSTRACT

The invention relates to novel compounds of the formula:

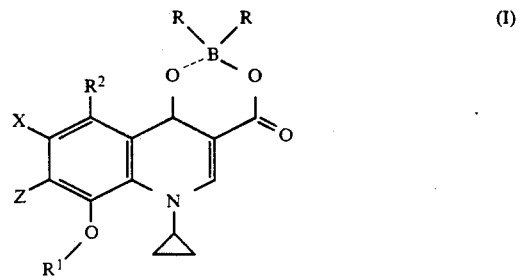

useful as an intermediate in the preparation of quinoline carboxylic acid medicaments.

1 Claim, No Drawings

(6,7)-SUBSTITUTED-8-ALKOXY-1-CYCLOPROPYL-1,4-DIHYDRO-4-OXO-3-QUINOLINECARBOXYLIC ACID-O3,O4) BIS (ACYLOXY-0) BORATE AND THE SALT THEREOF, AND THE PREPARING METHOD OF THE SAME

DETAILED DESCRIPTION OF THE INVENTION

Utilizable Field on the Industry

The present invention concerns a novel compound of the important intermediate for preparing a novel quinolonecarboxylic acid having an alkoxy group on 8-position thereof which is useful as a medicament, (6,7-substituted-8-alkoxy-1-cyclopropyl-1,4-dihydro-4-oxo-3-quinolinecarboxylic acid-$O^3,O^4$) bis (acyloxy-O) borate, the salt thereof, the hydrate thereof and method of preparation of the same.

Comparison with the Conventional Technique

As the preparing method of a quinolonecarboxylic acid derivative having an alkoxy group on 8-position thereof, there are two known methods as follows.

(1) (described in Japanese Patent Kokai Sho 62-252772)

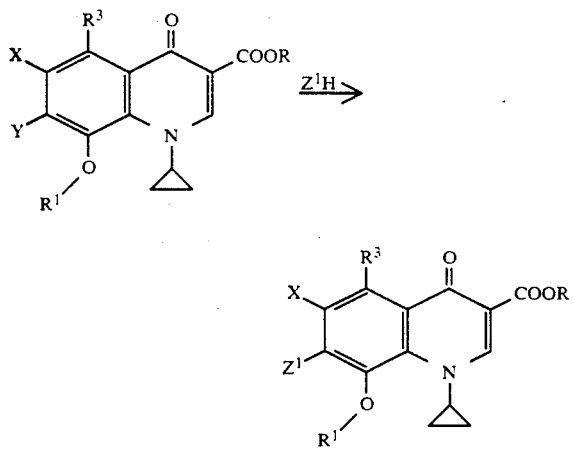

(2) (described in Japanese Patent Kokai Sho 63-198664)

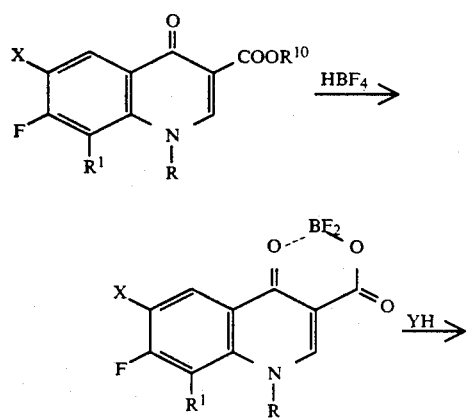

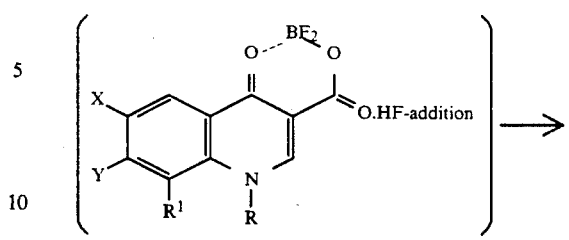

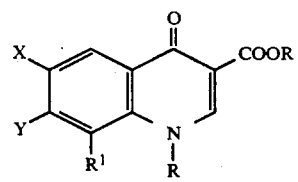

However, as in the method (1) there is an alkoxy group, an electron donating group, on 8-position thereof, the reactivity of 7-position thereof decreases and hence, in a mild reaction condition, the desired 8-alkoxyquinolonecarboxylic acid derivative can be obtained only at an extremely low yield. Furthermore, when making the reaction condition severe, the alkoxy group on 8-position undergoes dealkylation to become hydroxyl group and hence the desired product can not be obtained with high purity.

As the method (2) proceeds via a boron fluoride chelate compound, the aimed product can be obtained at high yield. Fluorinated boric acid, however, is so expensive that the cost becomes higher, and further, it is difficult to prepare it by means of usual equipment of industry, because hydrogen fluoride acid occurs as by-product at the time of preparing the intermediate.

Means to Solve the Problem

In these circumstances, as the result of strenuous investigation of the inventors of the present invention on the industrial preparing process of quinolonecarboxylic acid having alkoxy group on 8-position thereof, the present inventors have found that the above problem can be solved by employing (6,7-substituted-8-alkoxy-1-cyclopropyl-1,4-dihydro-4-oxo-3-quinolinecarboxylic acid-$O^3,O^4$) bis (acyloxy-O) borate, the salt thereof and the hydrate thereof represented by the general formula (I) as the intermediate.

In other words, not only the chelate compound of the present invention is suitable for the industrial preparation thereof because of not providing hydrogen fluoride acid as by-product which corrodes a reaction-pot and others at the time of the synthesis thereof, but also there is a feature that the aimed product can be obtained at high yield and with high purity by employing this chelate compound.

In addition, there is also a merit that it can be prepared at a cost extremely cheaper than in the known method.

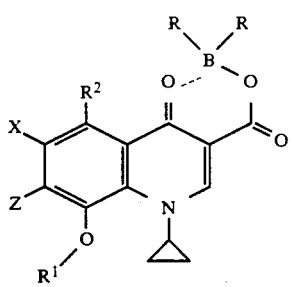

(wherein X denotes a halogen atom, R denotes an aliphatic acyloxy group having 2-6 carbon atoms, aliphatic acyloxy group having 2-6 carbon atoms optionally substituted with a halogen atom, or aromatic acyloxy group having 7-11 carbon atoms, $R^1$ denotes a lower alkyl group, $R^2$ denotes a hydrogen atom, halogen atom, amino group or nitro group, Z denotes a halogen atom,

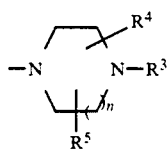

(herein n is 1 or 2, $R^3$ denotes a hydrogen atom, lower alkyl group, acyl group, alkoxycarbonyl group or aralkyl group, $R^4$ and $R^5$ each independently denote a hydrogen atom, lower alkyl group, substituted lower alkyl group, cycloalkyl group or phenyl group respectively) or

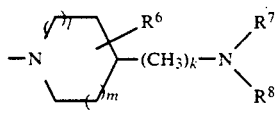

herein k is 0, 1 or 2, l is 0, 1 or 2, m is 0 or 1, $R^6$ denotes a hydrogen atom, halogen atom, lower alkyl group or hydroxyl group, $R^7$ denotes a hydrogen atom, lower alkyl group or substituted lower alkyl group, $R^8$ denotes a hydrogen atom, lower alkyl group, acyl group, alkoxycarbonyl group or aralkyl group) or azetidino group, pyrrolidino group, 3-hydroxypyrrolidino group, piperidino group, morpholino group or thiomorphorino group.

The chelate compound of the present invention can be prepared according to the following reaction process.

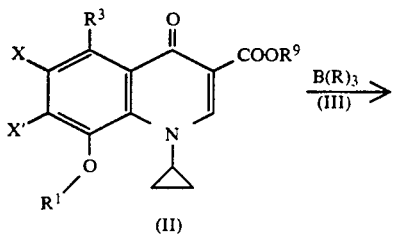

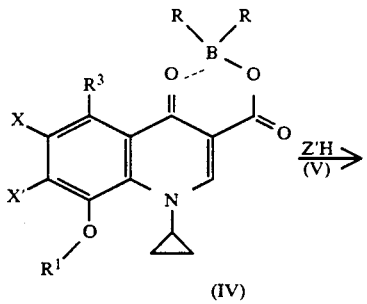

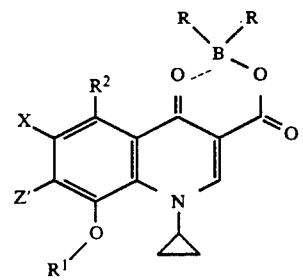

(wherein X' denote a halogen atom, $R^9$ denotes a hydrogen atom or lower alkyl group, X, R, $R^1$, $R^2$ are as mentioned above and Z' is one of Z in which a halogen atom is excluded from the definition of Z.

1) A compound of the general formula wherein Z is a halogen atom can be prepared by allowing a compound of the general formula (II) to react with triacyloxyborate derivative of the general formula (III) in the presence of solvent. The triacyloxyborate derivative of the general formula (III) can be employed in a quantity of 1-50 equivalents, preferably 5 equivalents to the compound of the general formula (II).

As a reaction solvent, an organic acid (for example, acetic acid, propionic acid, trifluoroacetic acid) can be employed. At this time, the reaction temperature is within a range of 20°-200° C., preferably a range from 20° C. to the boiling point of employed solvent. The triacyloxyborate derivative of the general formula (III) can be prepared by allowing boric acid to react in an organic acid (for example acetic acid, propionic acid, trifluoroacetic acid) or an organic acid anhydrate (for example, acetic anhydride propionic anhydride, trifluoroacetic anhydride) and in the presence of zinc chloride. A quantity of the employed boric acid is 1.1-2 equivalents, preferably 1.5 equivalents to the compound of the general formula (II). In this case, the obtained triacyloxyborate derivative, without being isolated, can be used for the reaction with a compound of the general formula (II).

2) A compound of the general formula (I) wherein Z is one other than a halogen atom can be prepared by allowing a compound represented by the general formula (IV) which is one of the general formula (I) wherein Z is a halogen atom to condensate with a cyclic amino compound represented by the general formula (V).

Z'H     (V)

(wherein Z' denotes

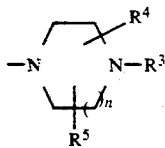

(herein n is 1 or 2, $R^3$ denotes a hydrogen atom, lower alkyl group, acyl group, alkoxycarbonyl group or aralkyl group, $R^4$ and $R^5$ each independently denote a hydrogen atom, lower alkyl group, substituted lower alkyl group, cycloalkyl group or phenyl group respectively) or

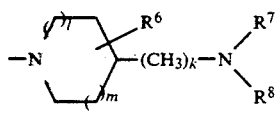

(herein k is 0, 1 or 2, l is 0, 1 or 2, m is 0 or 1, $R^6$ denotes a hydrogen atom, halogen atom, lower alkyl group or hydroxyl group, $R^7$ denotes a hydrogen atom, lower alkyl group or substituted lower alkyl group, $R^8$ denotes a hydrogen atom, lower alkyl group, acyl group, alkoxycarbonyl group or aralkyl group) or azetidino group, pyrrolidino group, 3-hydroxypyrrolidino group, piperidino group, morpholino group or thiomorpholino group.

The reaction of a compound of the general formula (I) wherein Z is a halogen atom with a cyclic amino compound represented by the general formula (IV) can be conducted without solvent or in the presence of a polar solvent such as water, alcohol, acetonitrile, dimethylformamide (DMF) dimethyl sulfoxide (DMSO), hexamethylphosphoric amide (HMPA), pyridine, picoline and so on.

The reaction temperature is optionally selected within the range from the room temperature to 200° C., preferably from room temperature to 100° C.

More in detail, it is suitable to allow a compound of the general formula (I) wherein Z is a halogen atom to react with 1-5 times mole of a cyclic amino compound represented by the general formula (IV) in 2-10 times vol of the above-mentioned solvent at a temperature from the room temperature to 50° C. for 1-50 hours. At this time, it is also preferable to employ triethylamine, diazabicyclo-base or potassium carbonate etc.

EXAMPLES

The examples are illustrated as follows to explain the present invention is more detail, but the present invention is not subjected to any restriction by these examples.

EXAMPLE 1

To a mixture of boric acid 57.2 g (0.925 mol) and zinc chloride 1.24 g was added acetic anhydride 300 ml, which was then subjected to stirring at 110° C. for 1.5 hours.

To this reaction mixture was added glacial acetic acid 400 ml and was further subjected to stirring for 1 hour at the same temperature.

After allowed to cool, ethyl 1-cyclopropyl-6,7-difluoro-1,4-dihydro-8-methoxy-4-oxo-3-quinolinecarboxylate 200 g (0.619 mol) was added thereto at a temperature of 50°-60° C. and afterwards glacial acetic acid 200 ml was added thereto, which was then subjected to the reaction for 5 hours.

The reaction mixture was concentrated under a reduced pressure, the oily residue was poured into 8 liter of icewater. The resulting precipitate was collected by filtration and suspended into 3 liter of water and collected by filtration, which was then dried to give (1-cyclopropyl-6,7-difluoro-1,4-dihydro-8-methoxy-4-oxo-3-quinolinecarboxylic acid-$O^3,O^4$) bis (acetate-O)-borate 249 g as light orange yellow powder.

Melting Point 113°-117° C.

Value of Elementary Analysis (%) (as $C_{18}H_{16}BF_2NO_8 \cdot \frac{1}{4}H_2O$).

Calculated Value C, 50.56; H, 3.89; N, 3.28.

Observed Value C, 50.32; H, 3.71; N, 3.33.

NMR spectrum (CDCl$_3$, δ) 1.13-1.60 (4H, m,), 1.92 (6H, S, —OCOCH$_3$), 4.2 (3H, d, J=2 Hz, —OCH$_3$), 4.33-4.73 (1H, m), 7.97-8.28 (1H, dd, J=8 Hz, 10 Hz, 5-H), 9.24 (1H, s, 2-H).

EXAMPLE 2

To (1-cyclopropyl-6,7-difluoro-1,4-dihydro-8-methoxy-4-oxo-3-quinolinecarboxylic acid-$O^3,O^4$) bis (acetate-O)-borate 12.3 g (29.1 m mol) was added a mixture of 2-methylpiperazine 4.38 g (43.7 m mol), triethylamine 8.2 ml and acetonitrile 30 ml, which as then subjected to stirring for overnight at the room temperature.

The residue obtained by distilling off the solvent was dissolved into ethyl acetate 40 ml. After washed with water, it was dried over anhydrous sodium sulfate. It was concentrated and dried up under reduced pressure to give [1-cyclopropyl-7-(3-methyl-1-piperazinyl)-6-fluoro-8methoxy-1,4-dihydro-4-oxo-3-quinolinecarboxylic acid-$O^3,O^4$] bis (acetate-O)-borate 12.9 g (yield 91.0%).

Melting Point 126°-129° C.

Value of Elementary Analysis (%) (as $C_{23}H_{27}BFN_3O_8 \cdot \frac{3}{4}H_2O$).

Calculated Value C, 53.45; H, 5.56; N, 8.13.

Observed Value C, 53.36; H, 5.46; N, 7.93.

NMR Spectrum (CDCl$_3$, δ) 0.84-1.47 (7H, m,), 2.04 (6H, s, —OCOCH$_3$), 2.47 (1H, =N—H), 2.82-3.66 (7H, m), 3.80 (3H, s, —OCH$_3$), 4.10-4.35 (1H, m,), 7.93 (1H, d, J=12 Hz, 5-H), 9.12 (1H, s, 2-H).

EXAMPLE 3

(1-cyclopropyl-6,7-difluoro-8-methoxy-1,4-dihydro-4-oxo-3-quinolinecarboxylic acid-$O^3,O^4$) bis (acetate-O)-borate 2.0 g, cis-3-λ-butoxycarbonylamino-4-methylpyrrolidine 1.4 g, acetonitrile 6 ml and triethylamine 1.6 g were charged and subjected to stirring at room temperature for 24 hours.

After dissolved into ethyl acetate, it was washed with water.

After dried over anthydrous sodium sulfate, it was concentrated and dried up to give [7-(cis-3-λ-butoxycarbonylamino-4-methyl-1-pyrrodinyl)-1-cyclopropyl-6-fluoro-8-methoxy-1,4-dihydro-4-oxo-3-quinolinecarboxylic acid-$O^3,O^4$] bis (acetate-O)-borate 2.8 g (yield 98.2%).

Melting Point 146°-148° C.

Value of Elementary Analysis (%) (as $C_{28}H_{35}BFN_3O_{10} \cdot 1\frac{3}{4}H_2O$).

Calculated Value C, 52.97; H, 6.11; N, 6.62.

Observed Value C, 53.01; H, 5.73; N, 6.57.

[1-Cyclopropyl-7-(3-methyl-1-piperazinyl)-6-fluoro-8-methoxy-1,4-dihydro-4-oxo-3-quinolinecarboxylic acid-$O^3,O^4$] bis (acetate-O) borate and [7-(3-amino-4-methyl-1-pyrrolidinyl)-1-cyclopropyl-6-fluoro-1,4-dihydro-8-methoxy-4-oxo-3-quinolinecarboxylic acid-$O^3,O^4$] bis (acetate-O)-borate prepared by the present invention can be converted into 8-alkoxyquinolonecarboxylic acid which is industrially useful by the following process.

REFERENCE EXAMPLE 1

To [1-cyclopropyl-7-(3-methyl-1-piperazinyl)-6-fluoro-8-methoxy-1,4-dihydro-4-oxo-3-quinolinecarboxylic acid-$O^3,O^4$] bis (acetate-O)-borate 14.2 g (29.1 m mol) was added a mixture of triethylamine 50 ml (0.36 mol), ethanol 264 ml and water 66 ml, which was then refluxed with stirring for 6 hours.

After the reaction solution was cooled, undissolved matter was filtered off, and the filtrate was concentrated and dried up to give yellow oily matter. It was dissolved with heating into ethanol 240 ml and, after cooled, the resulting precipitate was collected by filtration to give 1-cyclopropyl-7-(3-methyl-1-piperazinyl)-6-fluoro-8-methoxy-1,4-dihydro-4-oxo-3-quinolinecarboxylic acid 9.1 g (83.4%).

REFERENCE EXAMPLE 2

[7-(cis-3-λ-Butoxycarbonylamino-4-methyl-1-pyrrolidinyl)-1-cyclopropyl-6-fluoro-8-methoxy-1,4-dihydro-4-oxo-3-quinolinecarboxylic acid-$O^3,O^4$] bis (acetate-O)-borate 2.8 g was dissolved into dichloromethane and trifluoroacetic acid 40 ml was added dropwise thereto under water-cooling.

After stirring at the room temperature for 30 minutes, it was concentrated. After the residue was added with water 40 ml and neutralized by NaOH aqueous solution, it was subjected to extraction with ethyl acetate.

After the organic layer was washed with saturated saline water, it was dried over anhydrous sodium sulfate, and then concentrated and dried up.

With adding of ethanol 10 ml, it was dissolved with heating thereinto and, after cooled, the resulting precipitate was collected by filtration followed by being dried to give 7-(cis-3-amino-4-methyl-1-pyrrolidinyl)-1-cyclopropyl-6-fluoro-8-methoxy-1,4-dihydro-4-oxo-3-quinolinecarboxylic acid 1.0 g (57.4%).

Melting Point 214°–215° C.

What is claimed is:

1. A compound represented by a formula I

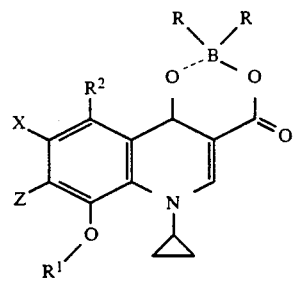

wherein X denotes a halogen atom, R denotes an alkanoyloxy group having 2–6 carbon atoms, alkanoyloxy group having 2–6 carbon atoms substituted with a halogen atom, or aromatic carboxylic acid acyloxy group having 7–11 carbon atoms, $R^1$ denotes a lower alkyl group, $R^2$ denotes a hydrogen atom, halogen atom, amino group or nitro group, Z denotes a halogen atom,

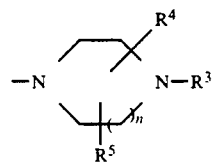

wherein n is 1 or 2, $R^3$ denotes hydrogen atom, a lower alkyl group, alkanoyl group, alkoxycarbonyl group or aralkyl group, $R^4$ and $R^5$ each independently denote a hydrogen atom, lower alkyl group, cycloalkyl group or phenyl group, or

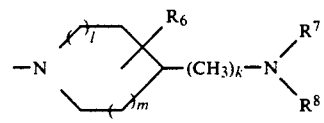

wherein k is 0, 1 or 2, l is 0, 1 or 2, m is 0 or 1, $R^6$ denotes a hydrogen atom, halogen atom, lower alkyl group or hydroxyl group, $R^7$ denotes a hydrogen atom or lower alkyl group, $R^8$ denotes a hydrogen atom, lower alkyl group, alkanoyl group, alkoxycarbonyl group or aralkyl group, or azetidino group, pyrrolidino group, 3-hydroxypyrrolidino group, piperidino group, morpholino group or thiomorpholino group, or a salt or hydrate thereof.

* * * * *